United States Patent [19]

Roessler et al.

[11] Patent Number: 5,176,670

[45] Date of Patent: Jan. 5, 1993

[54] DISPOSABLE DIAPER WITH IMPROVED MECHANICAL FASTENING SYSTEM

[75] Inventors: Thomas H. Roessler, Menasha; Bruce M. Siebers, Appleton, both of Wis.

[73] Assignee: Kimberly-Clark Corporation, Neenah, Wis.

[21] Appl. No.: 653,850

[22] Filed: Feb. 11, 1991

Related U.S. Application Data

[62] Division of Ser. No. 287,416, Dec. 20, 1988, Pat. No. 5,019,073.

[51] Int. Cl.$^5$ .................. A61F 13/15; A61F 13/20
[52] U.S. Cl. ..................... 604/391; 604/385.1; 604/389
[58] Field of Search .................... 604/378, 389–391, 604/385.1

[56] References Cited

U.S. PATENT DOCUMENTS

| | | | |
|---|---|---|---|
| 3,081,772 | 3/1963 | Brooks et al. | 128/287 |
| 3,110,312 | 12/1963 | Wirth | 128/287 |

(List continued on next page.)

FOREIGN PATENT DOCUMENTS

| | | |
|---|---|---|
| 7462574 | 4/1976 | Australia. |
| 672690 | 10/1963 | Canada. |
| 0013463A1 | 7/1980 | European Pat. Off.. |
| 0276970 | 8/1988 | European Pat. Off.. |
| 0287388A2 | 10/1988 | European Pat. Off.. |
| 319249A1 | 6/1989 | European Pat. Off.. |
| 321232A1 | 6/1989 | European Pat. Off.. |
| 321234A1 | 6/1989 | European Pat. Off.. |
| 324577A1 | 7/1989 | European Pat. Off.. |
| 324578A1 | 7/1989 | European Pat. Off.. |
| 2335165 | 7/1977 | France. |
| 2594650 | 8/1987 | France. |
| 2606257 | 5/1988 | France. |
| WO83/03754 | 11/1983 | PCT Int'l Appl.. |
| 1430747 | 4/1976 | United Kingdom. |
| 493819 | 11/1988 | United Kingdom. |
| 8602263 | 4/1986 | World Int. Prop. O. ......... 604/391 |

Primary Examiner—Randall L. Green
Assistant Examiner—R. Clarke
Attorney, Agent, or Firm—Paul Yee

[57] ABSTRACT

An article, such as a disposable diaper, which includes a refastenable mechanical fastener system for closing and opening the waistband. The fastener comprises a hook and loop system, such as a Velcro ® fastener system, developed for superior performance in fastening the waistband. The hook material of the fastener is molded of a copolymer of polypropylene which has flexural modulus of 70,00–120,00 psi; shore hardness D-40 to D-80 and the hooks are tapered base to tip, alternating hook design, of 0.04–0.05 inch caliper. The hook density in the material is about 740 hooks per inch on 40 rows to the inch on base film of 0.008–0.010 inch thickness. The loop material is a raised loop fabric of polyester fiber, two bar warp knit construction, with napped surface. The fabric is polyethylene terephthalate of basis weight in the range 1.0–3.0 ounce per square yard. The hook material is preferably mounted on the ears of the garment at the rear waistband which attaches to loop material. The loop material is mounted on the front waistband in one form of construction; or is adhesively backed and carried with the hook tabs to the front waistband where it adheres, the hook material being releasable and refastenable. The hook and loop fastener has peel force in the range of about 200–1200 gram per inch of width of fastener and shear of 6.60–20.0 pounds per square inch. In another form of the invention, a separate rear waistband is bonded to the rear margin of the diaper and such waistband has lateral ear portions with tabs of hook material attached. The waistband may be of elastomeric material for snug fit about the waist of the user. There are several other embodiments of diaper construction in the disclosure.

23 Claims, 9 Drawing Sheets

U.S. PATENT DOCUMENTS

| | | | |
|---|---|---|---|
| 3,141,461 | 7/1964 | Farris | 128/284 |
| 3,150,664 | 9/1964 | Noel | 128/287 |
| 3,180,335 | 4/1965 | Duncan et al. | 128/287 |
| 3,196,511 | 7/1965 | Kintner | 24/204 |
| 3,359,980 | 12/1967 | Rosenblatt | 128/284 |
| 3,441,024 | 4/1969 | Ralph | 128/287 |
| 3,460,535 | 8/1969 | Behna | 128/288 |
| 3,530,859 | 9/1970 | Heimowitz | 128/284 |
| 3,618,608 | 11/1971 | Brink | 128/287 |
| 3,630,201 | 12/1971 | Endres et al. | 128/287 |
| 3,653,381 | 4/1972 | Warnken | 128/284 |
| 3,882,871 | 5/1975 | Taniguchi | 128/287 |
| 3,955,575 | 5/1976 | Okuda | 128/284 |
| 4,047,530 | 9/1977 | Karami | 128/287 |
| 4,049,001 | 9/1977 | Tritsch | 128/287 |
| 4,050,463 | 9/1977 | Schaar | 128/287 |
| 4,051,854 | 10/1977 | Aaron | 128/284 |
| 4,145,763 | 3/1979 | Abrams et al. | 2/403 |
| 4,259,957 | 4/1981 | Sonenstein et al. | 128/287 |
| 4,338,938 | 7/1982 | Seavitt | 128/284 |
| 4,402,690 | 9/1983 | Redfern | 604/391 |
| 4,410,327 | 10/1983 | Baggaley | 604/391 |
| 4,445,242 | 5/1984 | Bowen | 5/484 |
| 4,475,912 | 10/1984 | Coates | 604/385 |
| 4,516,975 | 5/1985 | Mitchell | 604/385 |
| 4,568,342 | 2/1986 | Davis | 604/391 |
| 4,578,073 | 3/1986 | Dysart et al. | 604/397 |
| 4,597,760 | 7/1986 | Buell | 604/397 |
| 4,597,761 | 7/1986 | Buell | 604/397 |
| 4,610,680 | 9/1986 | LaFleur | 604/385 |
| 4,617,022 | 10/1986 | Pigneul et al. | 604/391 |
| 4,680,030 | 7/1987 | Coates et al. | 604/391 |
| 4,681,581 | 7/1987 | Coates | 604/391 |
| 4,704,117 | 11/1987 | Mitchell | 604/391 |
| 4,728,326 | 3/1988 | Gilles | 604/391 |
| 4,745,926 | 5/1988 | Hlusko | 128/134 |
| 4,761,318 | 8/1988 | Ott et al. | 428/85 |
| 4,770,917 | 9/1988 | Tochacek et al. | 428/95 |
| 4,773,906 | 9/1988 | Krushel | 604/391 |
| 4,778,701 | 10/1988 | Pape et al. | 604/389 |
| 4,794,028 | 12/1988 | Fischer | 428/100 |
| 4,801,298 | 1/1989 | Sorenson et al. | 604/384 |
| 4,834,742 | 5/1989 | Wilson et al. | 604/389 |
| 4,857,067 | 8/1989 | Wood et al. | 604/389 |
| 4,869,724 | 9/1989 | Scripps | |
| 4,936,840 | 6/1990 | Proxmire | 604/391 |
| 4,963,140 | 10/1990 | Robertson et al. | 604/391 |
| 4,973,326 | 11/1990 | Wood et al. | 604/391 |
| 4,994,054 | 2/1991 | Pigneul et al. | 604/391 |

DISPOSABLE DIAPER WITH IMPROVED MECHANICAL FASTENING SYSTEM

This is a divisional application of copending U.S. patent application Ser. No. 07/287,416, filed on Dec. 20, 1988, now U.S. Pat. No. 5,019,073.

The invention relates to an absorbent article, such as a diaper, incontinent garment or the like, and more particularly to an improved fastening system for securing the placement of the absorbent article on the body of the user.

BACKGROUND OF THE INVENTION

Various fastening devices for disposable diapers have been employed for fastening the waistband portion about the torso of the user. Among these are adhesive fastening devices, such as shown in U.S. Pat. Nos. 3,180,355; 3,630,201; 4,047,530; 4,049,001; 4,050,453 and French Patent 7,436,169. The fastening device generally comprises an adhesive tab attached to the outer (backing) sheet of the diaper at the rear portion and the active adhesive surface of the tab is stuck onto another portion of the backing sheet surface near the front portion thereby closing the diaper. The adhesive system of diaper closing may need repeated reopening and reclosing to check the user's condition or whether the diaper needs changing. In use, the diaper may stretch or otherwise become loosened, thereby resulting in applying the adhesive portion of the tab in a new zone on the backsheet surface. Failure of the diaper may result if the tab adhesive becomes contaminated with baby powder, oil or the like; or should the tab and backsheet adhesion result in a tear of the area where the tab is initially applied. The torn area of the backsheet of the diaper will stay adhered to the tab. In either event, the reclosing of the diaper is ineffective, at least insofar as that tab is concerned, which results in premature failure of the diaper and its unnecessary disposal.

The problem of tearing the backsheet (liquid-impermeable) material by unfastening of the adhesive tab has been dealt with by providing a region of reinforcement on the backsheet in the normal landing zone for the tab of the adhesive surface.

Mechanical fastening systems have been devised which provide for repeated refastening of the diaper garment, such as is disclosed in copending application, U.S. patent application Ser. No. 089,660, filed Aug. 25, 1987, and owned by the assignee of the present application. The fastening system of the copending application utilizes a plurality of cooperating snap fasteners along the sides of the diaper extending in their fixed point placement in the span from the waistband to the leg opening, and the snap fasteners provide a primary closure of the garment on the wearer along the sides in the waist-to-leg span. This is supplemented by a secondary closure effecting a continuous closure between the spaced-apart snap fasteners and provide a full length fastening in the span from the waist to leg region. The secondary closure is disclosed as cohesive adhesive strips in one form, or as an alternative a hook and loop fabric fastener tape, referred to as Velcro ® fastener materials, placed between the snaps and along the tape extending on the sides of the diaper between waistband and leg opening. The hook and loop fastener is disclosed as a "Velcro-type fastener", which provides the means for securing the waistband around the body of the wearer. Another mechanical system for diaper closing is described in a published French Patent Application No. 2,594,650, in which there is generally disclosed an arrangement of tabs attached to the ends of the rear waistband provided with hook fasteners which fasten to a strip of loop material attached to the exterior surface at the front of the diaper.

SUMMARY OF THE INVENTION

The invention is directed to a hook and loop mechanical fastener system, such as a Velcro-style fastener, specifically developed for disposable garments, in particular disposable diapers and incontinent garments. The hook and loop materials are lightweight, and provide a secure fastener system capable of refastening securely at least three times for opening and reclosing the garment. The invention provides a mechanical fastening system that possesses flexibility, softness and is low cost to produce; yet resists contamination that will interfere with its function as a fastener, and is adaptable to a wider range of sizes or girth of the user.

In specific form, the hook and loop fastener components as developed under the invention are according to the following:

The hook material is molded polyolefin, preferably polypropylene copolymer of flexural modulus from 70,000 to 20,000 PSI, which provides the proper stiffness of the hooks The material has shore hardness of D-40 to D-80. The hook design is tapered base to top with alternating hook design, hook density of 440-1040 hooks per inch, with preferred row density of about 20-60 rows per inch. The base polyolefin film of the hook material is from about 0.005 to 0.025 inches thick, and preferably is within the range of about 0.008 to 0.010 inches thick.

The loop material is a fabric of raised loop construction, stabilized through napping and thermosetting such that the loops are erect from the base material. The fabric is two bar warp knit construction having from 21 to 41 courses per inch and from 26 to 46 wales per inch, preferably of polyester yarn in which 15-35% of the yarn is composed of yarn having about 15 or less filaments and having a yarn denier within the range of about 15-30d. In addition, about 65-85% of the yarns are those having 10-30 individual filaments therein and having a yarn denier within the range of about 30-50d. The caliper is 0.010 to 0.040 inch and basis weight from 1.0 to 3.0 ounces per square yard.

The aforementioned hook and loop fastener provides fastener characteristics of 6.60 to 20.00 psi shear strength; 200 to 1200 grams per inch peel strength and has a minimum of three refastening functions. In practice, the fastener of the foregoing design has capability of 5 or more refastening cycles at the performance characteristics given above.

The invention provides for use and execution of the mechanical fastener in a variety of garment configurations, designs and uses, some of which are given hereinafter by way of preferred examples.

For a further understanding of the present invention and the objects thereof, attention is directed to the drawings and brief description thereof, to the detailed description of the preferred embodiments and to the appended claims.

DETAILED DESCRIPTION OF THE INVENTION

The detailed description of the invention is made in connection with preferred embodiments of the invention and in the context of an absorbent disposable diaper article. The described structures of mechanical fasteners would be suitable for and applicable to other forms of absorbent articles or articles, such as incontinent garments and the like.

Figure 10:
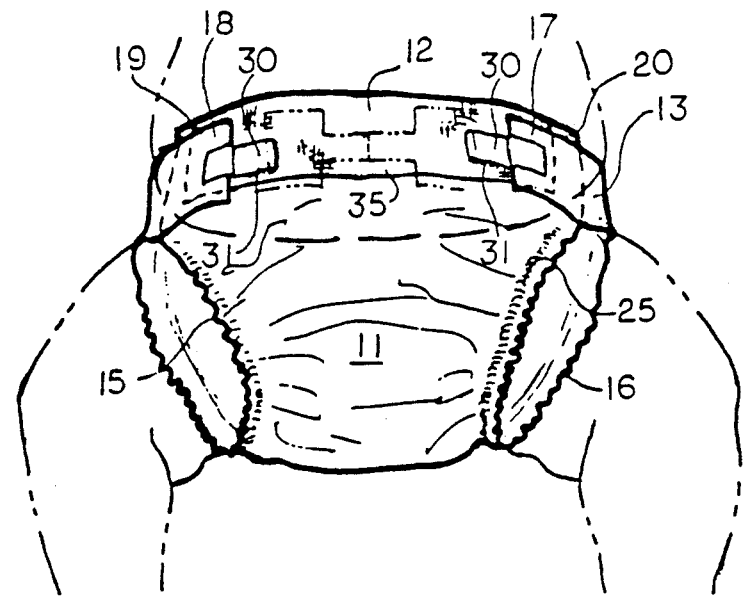
FIG. 10 is a perspective view of the diaper and fastening system of the invention as it is applied to the torso of a wearer.

Referring to FIGS. 1-4, a disposable absorbent garment 10, such as a disposable diaper article, comprises an elongated backsheet or outer cover 11 having front and rear waistband portions 12 and 13, respectively, at each longitudinal end. The intermediate portion 14 interconnects the waistbands A pair of leg openings are delimited along the marginal portions of each lateral side edge 15 and 16 of the outer cover 11. Ear portions 17-20 are delimited at each corner of the outer cover and blend with the leg openings. Upon placement of the garment 10 about the body of a user, such as a baby (FIG. 10), the longitudinally opposed ears, such as 17 and 20 and 18 and 19 overlap one another, or are engageable with each other, to complete the waistbands 12 and 13 encircling relationship about the torso of the wearer.

The backsheet layer 11 is a liquid-impermeable, substantially inelastic material, such as a polymer film. Examples are polyethylene film and polypropylene film of suitable thickness for flexibility, for example in the range of about 0.75 to 1.5 mils thickness, and is preferably about 1.0 mil. Another example of the backsheet 11 is a layer of a liquid impermeable, but vapor permeable, material such as a breathable, microporous film. Still further examples of backsheet material may comprise a nonwoven, fibrous web which has been suitably constructed and arranged to be substantially liquid impermeable. This nonwoven fibrous web may also be constructed to be liquid impermeable but vapor permeable. Such nonwoven fibrous web may be stretchable, and may be treated with a selected polymer coating or film to provide a desired degree of liquid impermeability and vapor permeability.

Figure 2:
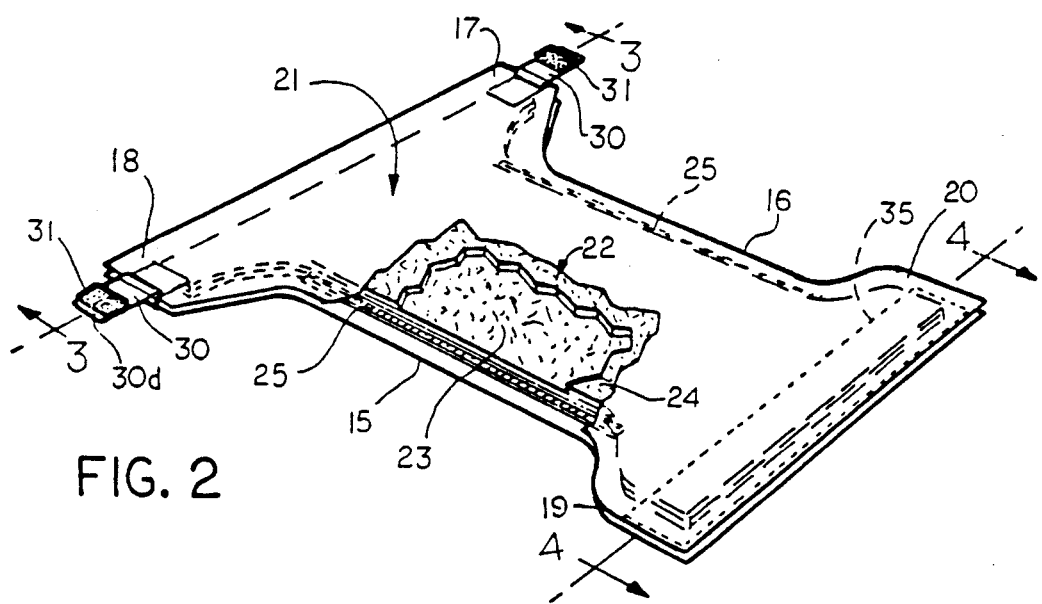
FIG. 2 is a perspective view showing the inside face of the diaper illustrated on FIG. 1.
Figure 3:
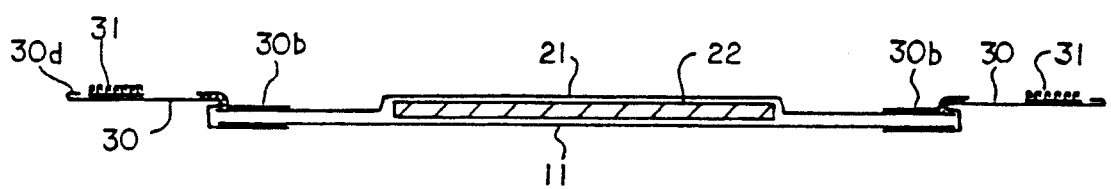
FIG. 3 is a sectional elevational (partly schematic) view taken along line 3—3 on FIG. 2.

As shown on FIG. 2, the inside liner sheet, or topsheet element 21 of the diaper article 10, is similar in size and contour to the backsheet element 11. This topsheet 21 is typically comprised of a liquid-permeable, elastic or inelastic and substantially hydrophobic material, for example a spunbonded web of synthetic polymer filaments or meltblown web or bonded carded web of synthetic polymer filaments. Suitable synthetic polymers include polyethylene, polypropylene and polyesters.

An absorbent body, generally indicated at 22 (FIG. 2), is structured and superposed on backsheet 11. The absorbent body 22 may comprise a pad 23 composed of airlaid, cellulosic fibers, such as wood pulp fluff, having density in range of 0.05–0.20 gram per cubic centimeter, and are sufficiently flexible to readily conform to the body of the wearer. As an alternate form, absorbent body 22 may be comprised of a coform material comprising a mixture of cellulose fibers and synthetic material polymer fibers; such as an airlaid blend of cellulosic fibers and meltblown polyolefin fibers (polyethylene and polypropylene fibers being two compositions of the polyolefins). The absorbent body 22 may also include an effective amount of an inorganic or organic high absorbency material to enhance absorptive capacity. Suitable inorganic high-absorbency materials include, as examples, absorbent clays and silica gels. Organic high-absorbency materials include, as examples, pectin, guar gum, and peat moss, as well as synthetic materials, for example, synthetic hydrogel polymers, such as carboxymethylcellulose, alkali metal salts of polyacrylic acids, polyacrylamides, polyvinyl alcohol, ethylene maleic anhydride copolymers, polyvinyl ethers, hydroxypropyl cellulose, polyvinyl morpholinone, polymers and copolymers of vinyl sulfonic acid, polyacrylates, polyacrylamides polyvinyl pyridine, and the like. Still other suitable polymers include hydrolyzed acrylonitrile grafted starch, acrylic acid grafted starch, and isobutylene maleic anhydride copolymers, and mixtures thereof. The hydrogel polymers are preferably lightly crosslinked to render the materials substantially water-insoluble.

Absorbent body 22 may also include a tissue wrap layer 24 to help maintain the integrity of the fibrous structure 23 This tissue wrap typically comprises a hydrophilic cellulosic material, such as creped wadding or a high wet-strength tissue. The diaper may also include additional components to assist in the distribution and storage of waste material. For example, the diaper may include a hydrophobic transport layer, such as described in U.S. patent application Ser. No. 109,784, filed Oct. 16, 1987 of S. Meyer, et al., entitled "Absorbent Article Having a Hydrophobic Transport Layer" of common ownership with the present application.

In the embodiment illustrated, as is a typically constructed article, the waist portions 12 and 13 may be provided with an elastic (not shown). This is comprised of a clothlike nonwoven fibrous material, such as an elastomeric stretch-bonded laminate. As an example, suitable meltblown elastomeric fibrous webs for forming waist elastic are disclosed in U.S. Pat. No. 4,663,220. Composite fabrics of at least one layer are described in European Patent Application No. 0 110 010 (Apr. 18, 1987). The composite nonwoven fabrics are commonly referred to as stretch-bonded laminates. Another material suited for use in the waistband elastic material is a heat shrinkable elastic film of three layer construction. The skin layers are composed of duPont Surylon, Gulf 2491T, Techmer 1094 E16, and duPont Conpol 8719-3. The core layer is composed of Pebax 3533SA00. The core layer is approximately 80% (by vol.) of the film.

The leg openings, at the lateral sides 15 and 16, are provided with elastic elements 25 implanted adjacent the said sides. The leg elastics may be comprised of synthetic and organic elastic film ribbons and used to shirr the leg margin of the garment. Suitable materials for this purpose include, by way of example, natural rubber, or polyurethane materials.

The intermediate portion 14 of the diaper 10 is narrower than the waistband portions 12 and 13. As such, the diaper 10 has a generally hourglass shape in plan view. The two ear sections 17 and 18 at the rear waistband portion 13 include tape tabs 30 for fastening the rear waistband 13 onto the front waistband 12 about the body of the wearer.

Figure 4:
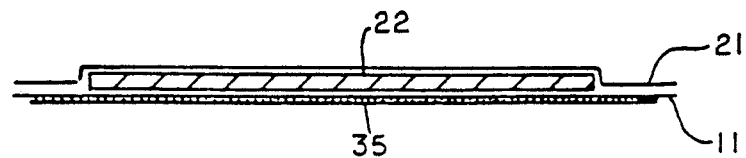
FIG. 4 is a sectional elevational (partly schematic) view taken along line 4—4 on FIG. 2.
Figure 5:
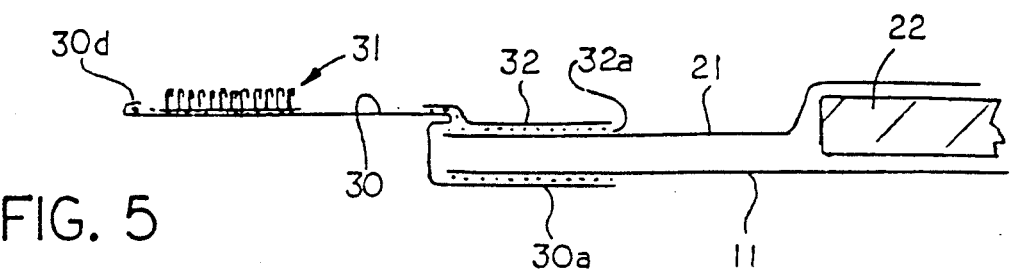
FIG. 5 is an enlarged view of the tab of the article on FIG. 3 assembled in its operative position of the mechanical fastener and showing the hook material exposed for attachment with the loop material.

The means attached to the diaper for fastening the front and rear waistbands to each other in an overlapping relationship for encircling the abdomen of the user comprise a hook and loop fastener made up of hook material and loop material components. With reference to FIG. 5, the tape of tabs 30 includes adhesive part 30a and separate tape piece 32 which are adhered together and extend along opposite surfaces of the ear portions 17 and 18. An example of the material for the tab structure is 4.5 mil polypropylene film with titanium dioxide filler (white) Another suitable material for the tab is a 2.0 ounce per square yard spunbond of polypropylene, which provides a porous substrate. The inboard sections of the tape pieces 30a and 30b are fastened onto the backsheet 11 and topsheet 21. respectively, at this point to secure the tabs 30 firmly to the ear portions 17 and 18 of the diaper. The backsheet and topsheet are firmly fastened together at this region in the fabrication of ear portions 17-20. This comprises one preferred form of fastening tabs 30 onto the diaper. On the drawings, FIGS. 3-9, the adhesive or bonded areas are schematically shown by the pattern of dots. With the various components of the diaper assembled in the article shown on FIG. 2, they are connected together, as a composite article, by heat bonding, hot melt adhesives or sonic bonds in one of the known techniques for fabrication.

Tabs 30 each include an outboard portion extending beyond the margin of the ears 17 and 18 of the backsheet. The outboard portion of the tab surface is provided with hook tab material 31 bonded to the tape. The free end portion of tab 30 may optionally be folded upon itself at 30d which provides a lift portion at the end of the tape and adjacent hook area 31. This end 30d provides a finger grip or lift for grasping and releasing the hook material by peeling it from its attachment on the loop material of the fastener. As may be seen on FIG. 6, the tab 30 may be folded inwardly to an inactive storage position whereat the hook material lightly attaches to the nonwoven material of topsheet 21.

The Hook Material

The hook material is produced from a process of continuous injection molding of a polymeric material, such as a polypropylene copolymer. It has been determined that the proper stiffness of the material is obtained from the copolymer having flexural modulus of 70,000-120,000 psi and shore hardness value within the range of about D-40 to D-80, preferably about D-61.

Figure 1:
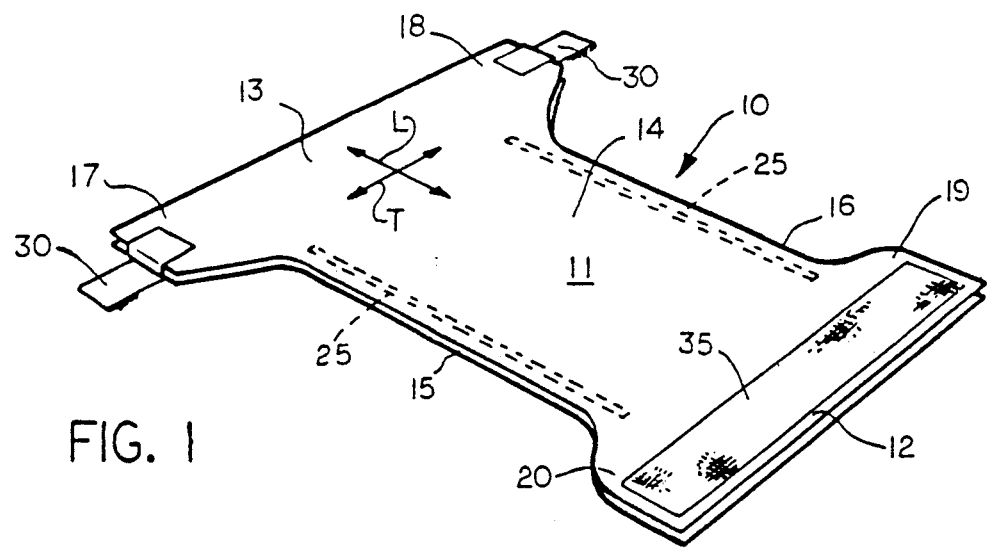
FIG. 1 is a perspective view of the outside face of a disposable diaper which incorporates a first embodiment of the present invention.
Figure 20:
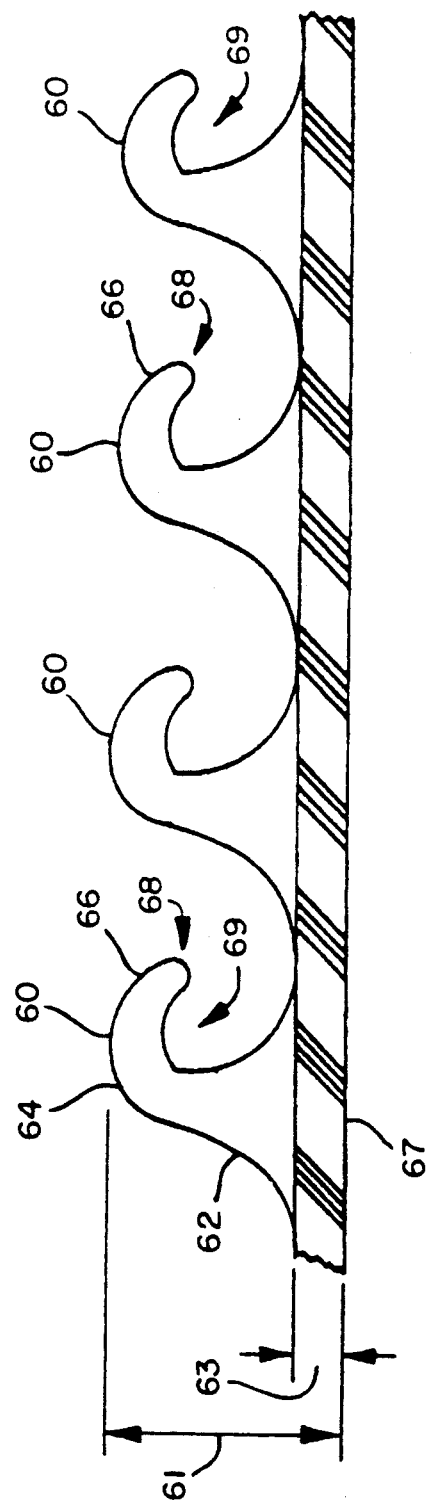
FIG. 20 representatively shows an enlarged, side-elevational view of hook material employed in the present invention.

The base strata of the hook material is assembled onto the surface of the tab 30 by adhesive, heat bonding or sonic welding to provide the J-shaped hooks in a configuration facing outwardly of the tab structure. As representively shown in FIG. 20, hooks 60 are tapered from base 62 to top 64 with the tips 66 of the hooks rounded with a discrete radius 68. The radiused tips are substantially without sharp edges which could excessively abrade and irritate a wearer's skin. As a result, the hook material employed in the present invention can be more "user-friendly". Preferably, the hook material has an alternating hook design wherein immediately adjacent rows of hooks (not shown) have the "mouth" openings 69 of the hooks facing in opposite directions. The alternating hook design can provide more uniform fastening and securement in all directions. If one desires a more "directional" securement with greater fastening force along one direction than another, the hook material can be configured with all of the hooks opening along substantially the same direction. A specific example of a suitable hook is the HTH #707 available from Velcro U.S.A. The overall thickness 61 (caliper) of the hook material is in the range of about 0.035 to 0.050 inch, and preferably about 0.045 inch. The hooks are attached to a base film 67 which has a thickness 63 in the range of about 0.005 to 0.025 inch, preferably a thickness in the range of about 0.008 to 0.010 inch. The hook density on the base is within the range of about 440 to 1040 hooks per square inch; preferably a hook density of about 740 hooks per square inch, as a particular example, hook material having a row density within the range of about 20-60 rows to the lineal inch of width, preferably a row density of about 40 rows per lineal inch. The material used may be clear or opaque with selected color of the material. The hook material is produced on rolls which range from 0.25 to 4.0 inches in width. Roll of ½ inch width material is preferred. The hook sections 31 placed on the tab 30 are cut to size of approximately ½ by 1 inch and bonded on the tab 30. In the example of this embodiment, tab 30 is approximately 1 inch wide. Referring to FIG. 1, the width of tab 30 lies in the longitudinal direction L on the diaper, accordingly, the hook material 31 is oriented such that, per the example given, the one inch dimension is in the direction L, the ½ inch dimension being in the transverse direction T.

The Loop Material

Figure 21:
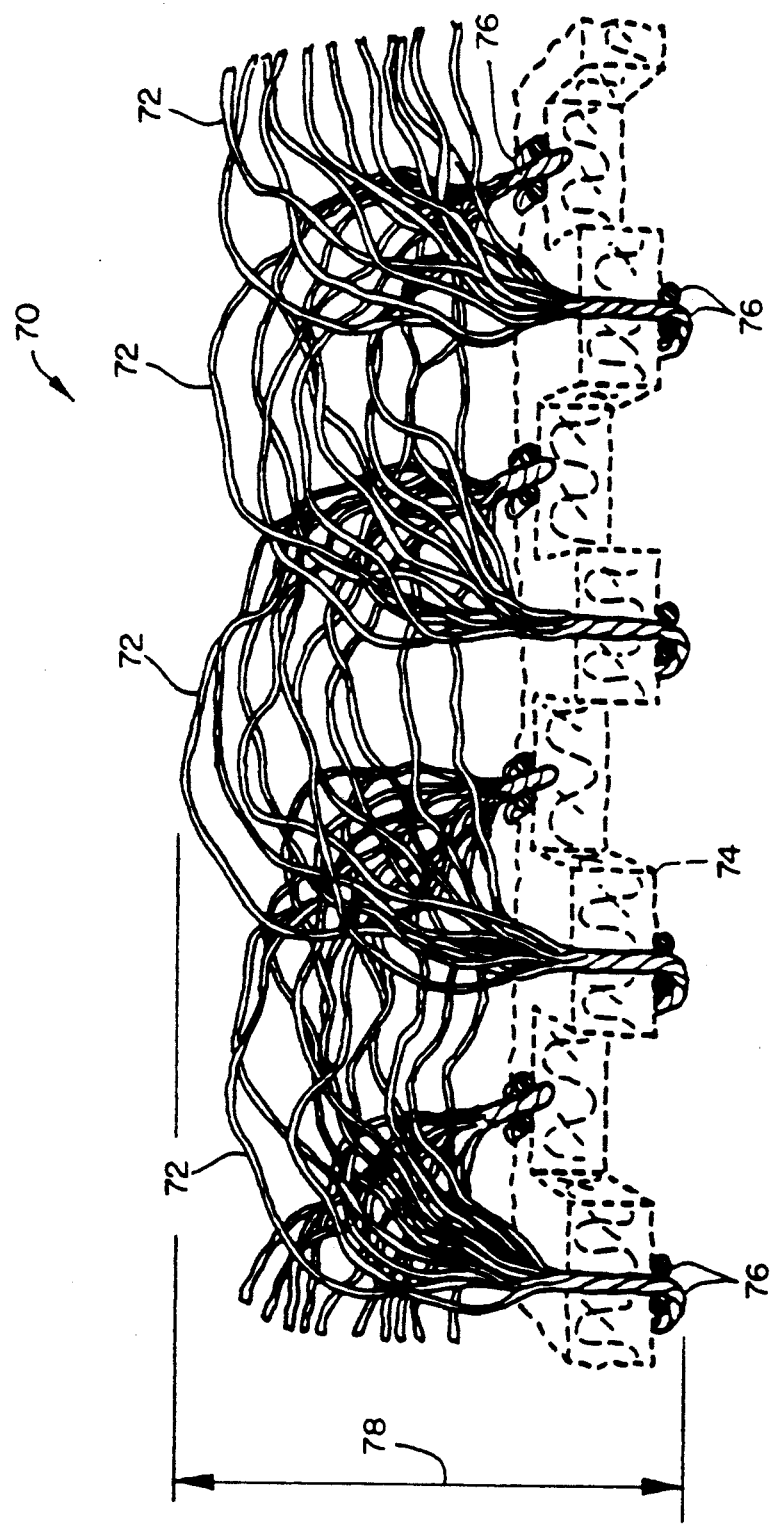
FIG. 21 representatively shows an enlarged, side-elevational view of loop material employed in the present invention.

As representively shown in FIG. 21, the loop component of the hook and loop fastener is a fabric material 70 comprising yarns 76 arranged to provide a raised loop construction in which the fabric is stabilized (loops 72 are erect from the fabric's base 74) through napping. Additionally, the loop material may be thermoset to impart other properties, such as is set forth in U.S. Pat. Nos. 3,475,926 issued Nov. 4, 1969 to J. Ruckstuhl and 3,090,097 issued May 21, 1963 to J. Ruckstuhl.

Preferably, a material of polyolefin based fibers or other synthetic fibers is used; an example of the fabric being a tricot polyester. More specifically, polyethylene terephthalate (PET) fiber mix in which about 15-35% of the fabric yarns are yarns composed of 1-15 filaments with the yarn having a denier within the range of about 15-30d, and about 65-85% of the fabric yarns are yarns having about 10-30 filaments per yarn and having a yarn denier within the range of about 30-50d comprises the fibers used in the fabric. Two bar warp knit construction is preferred in which courses are in the range 21-41 per inch and wales are in the range 26-46 per inch. The surface of the fabric is napped. The thickness caliper 78 is within the range of about 0.01 to 0.04 inch, the preferred caliper being about 0.035 inch. The basis weight of the fabric is in range of 1.0 to 3.0 ounces per square yard; the preferred basis weight being about 1.6 ounces per square yard. The fabric is printable or decoratable directly, or in the alternative may be laminated over a predecorated film base, whereby a print pattern shows through the loop material. Loop material is applied onto the front waistband portion 12 in a patch or swatch 35 with the loops erect and facing outwardly from the face of the back sheet 11 (FIG. 4). The extent of patch 35 may be varied and may take one of several geometric shapes, such as rectangular, irregular shape, diamond, triangle, circle, oval, chevron or the like. One further example of this variable is included in the drawings on FIG. 12, which is hereinafter described. In this regard, the loop material may also be configured as a plurality of patches. The plural patches (two or more) form a landing zone for the hook tabs which are composed of multiple, separate sections. The variation of shape or configuration of multiple patches will lend itself to desired function and size for fastening the waistband about the various sizes of users.

As is shown on FIG. 1, the preferred patch 35 is a rectangular piece cut from a running roll or web of the fabric to size so that the patch extends in the waistband 12 intermediate the ear portions 19 and 20. In the example given above, the patch may be on the order of 2 inch width by 8-10 inches of length. Patch 35 is fastened on the exterior surface of the back sheet 11 by known techniques, such as hot melt adhesive patterned onto the surface in dots, strips or bars, or fastened by heat bonding. Thus applied, the loop fabric patch 35 is preferably placed in the proximity of the lateral margin of the diaper at its one longitudinal end (depending upon whether elastic is placed along the waistband at this end portion) which corresponds with the front waistband 12 of the article.

Using the hook and loop materials referred to above, the mechanical fastener for the absorbent article provides performance characteristics per the following:
SHEAR FORCE: about 6.60-20.0 psi
PEEL FORCE: about 200-1200 (grams per inch of fastener); preferred is about 400-600 grams per inch
REUSES: Minimum of 3 times normally Minimum of about 3-7 times [refastening uses]; Desirable is 5 times "Shear" is determined according to ASTM Designation: D3654-82, "Standard Test Method for Holding Power of Pressure-Sensitive Tapes", which is incorporated herein by reference, and subject to the following modifications: In relation to the test, the closure is placed under an increasing load. The system being tested is a hook and loop closure system. (See 1. Scope) The apparatus should include an "INSTRON" or equivalent continuous rate of extension (CRE) tensile tester. (See 3. Apparatus) In carrying out the procedure (See 6. Procedure), test direction of the materials should be noted. The test materials are rolled five cycles (1 sq. in.), where one cycle equals once in each direction. The hook material is clamped into the upper jaw and the loop material clamped into the lower jaw of the Instron tensile testor. The engaged system (hook and loop) is pulled until failure. In doing the calculations (See 10. Calculations), the peak load is determined and recorded in grams.

"Peel" is determined according to ASTM Designation: D1876-72, "Standard Test Methods for Peel Resistance of Adhesives (T-Peel Test)", which is incorporated herein by reference, and subject to the following modifications:

4.1 No test panels are used; hook and loop materials are directly engaged and are not mounted on any other substrate unless specified. Test direction of the materials should be noted. No panels are used. The engaged test materials are rolled five cycles; where one cycle equals once in each direction. The hook material is clamped into the upper jaw and the loop material is clamped into the lower jaw.

In a suitable hook and loop fastening system, the fastener has a total resistance of at least about 150 gm. and preferably has a total peel resistance of at least about 400 gm. The total shear force resistance of the fastener is at least about 750 gm. and preferably is at least about 1000 gm. It should be readily recognized that a suitable fastening system will include a selected balance between the properties of total peel resistance and total shear force resistance. For example, a system with the lower values of peel resistance could be more suitable if the system also exhibited a higher total shear force resistance.

For the purposes of the present description, the total peel resistance value corresponds to the peel force determined in accordance with ASTM D1876-72 multiplied by the transverse width of engagement between the hook material and the loop material employed in the particular fastening system. Similarly, the total shear force resistance value corresponds to the shear stress determined in accordance with ASTM D3654-82 multiplied by the area of engagement between the hook material and loop material of the fastening system.

Referring to FIG. 5, the tabs 30 are shown extended with the hooks 31 facing upwardly. In this position, the diaper article 10 is installed on the wearer (see FIG. 10). The respective tabs 30 on the rear waistband are brought around the abdomen of the baby and the hooks 31 thereof pressed onto the loop material of the patch 35 to close the waistband in a snug position encircling the abdomen. The shirred elastics 25 at the side margins 15 and 16 each encircle a leg of the wearer to provide a good fit of the diaper. The placement of the two hook tabs 31 may vary between the extremes shown on FIG. 10, the solid outline representing a larger size waist and the dotted outline illustrating the smaller size waist for the user of the garment. The diaper may be opened by grasping the end 30d of the tabs 30 and lifting the hooks 31 free from the loop material 35, and thereafter refastened by again pressing the hooks 31 onto a selected zone of the patch 35.

Figure 6:
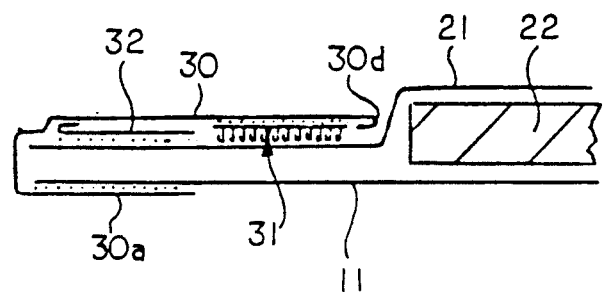
FIG. 6 is an enlarged view, similar to FIG. 5, showing the tab folded inwardly in position of storing the hook material of the fastener.
Figure 7:
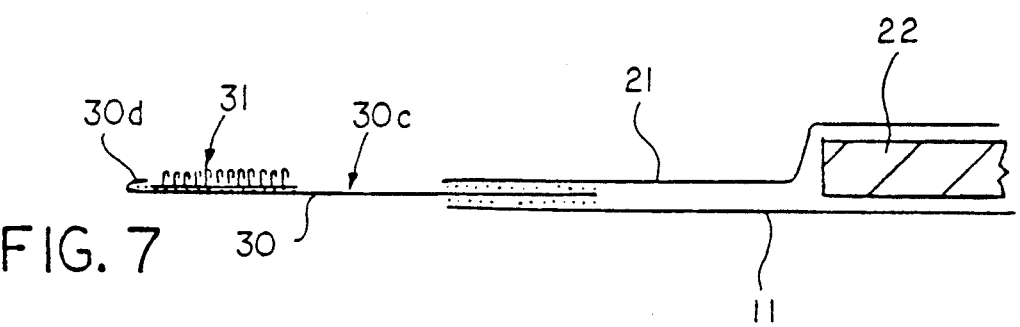
FIG. 7 is a sectional elevational view of a portion of the article of FIG. 2 illustrating another means of attaching the tab of the fastener to the diaper article in which the inboard end of the tape is laminated between the outer cover or backsheet of the diaper and the topsheet which is placed next to the wearer's skin.
Figure 8:
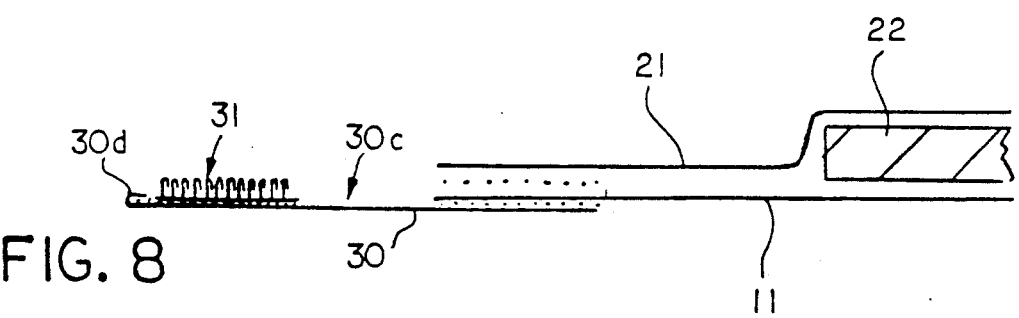
FIG. 8 is a view similar to FIG. 7 showing an alternative manner of attachment of the tab to the diaper in which the inboard portion of the tape is laminated with the outer cover sheet of the diaper.
Figure 9:
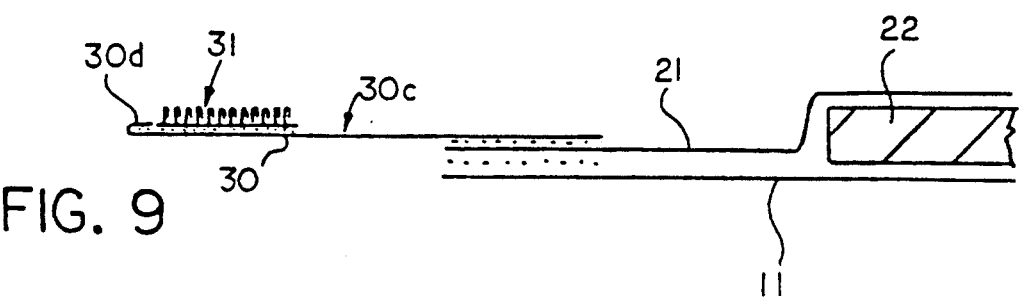
FIG. 9 is also a view similar to FIG. 7 showing another manner of attachment of the tab to the diaper in which the inboard end of the tape is laminated with the topsheet of the diaper.

FIG. 6 illustrates the folded position of the garment in which the tabs 30 are folded inwardly. This position places the hook material inwardly of the ear portions and hooks 31 are facing the topsheet 21 at a storage position, i.e. the hooks are exposed to lightly grip the topsheet material 21 when the diaper is packaged prior to use. When ready for use the tabs are folded outwardly to a position like that on FIG. 5 by grasping the end 30d of the tab FIG. 7-9 illustrate other variables for attaching the tabs 30 onto the diaper. FIG. 7 illustrates the attachment means whereby the tab 30 is inserted between the backsheet 11 and topsheet 21. The tab is there adhesively secured between the layers 11 and 21 by a hot melt adhesive applied in dot pattern or the like. The backsheet and topsheet are firmly fastened together with the tab between them in forming the laminated ear portion of diaper 10.

FIG. 8 illustrates an alternative attachment means in which the topsheet 21 and backsheet 11 are fastened together, such as by adhesive or by heat bonding in known manner. The tab 30 is attached to the exterior surface of the backsheet 11 by hot melt adhesive or heat bonding. The lamination of the three layers 21, 11 and 30 may be accomplished in one step, or accomplished separately.

FIG. 9 illustrates another means of attachment of the tabs 30 onto the topsheet 21 of the diaper where topsheet 21 and backsheet 11 are laminated to each other.

The tabs 30 are generally attached to the diaper ear portions, as illustrated on FIGS. 5 and 7-9 such that tab 30 extends laterally about 0.5 to 3.5 inches and preferably extends about 1.5 to 3 inches past the outside edge of the diaper ear portion. In this arrangement, the minimum girth dimension the diaper will fit is determined at the point where the tabs butt against each other, as is shown in the dotted outline on FIG. 10. The maximum waist girth dimension is the point at which the tabs 31 are positioned at the outer opposite edges of the loop fabric 35 so that all of the hook material area of the tab is positioned on and engages loops of the patch 35.

Figure 12:
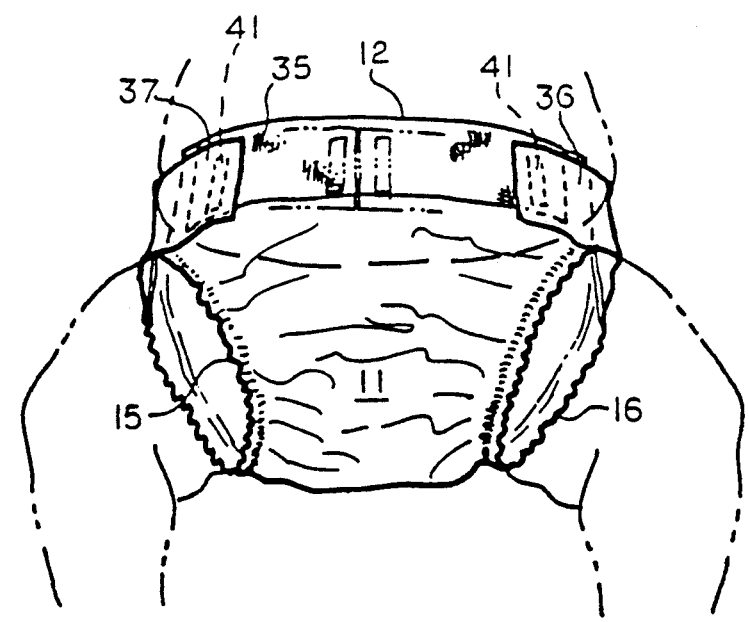
FIG. 12 is a perspective view of a disposable diaper on the torso of a wearer constructed as the second embodiment of the invention illustrating the increase of the adjustable size range of the diaper on the wearer of the article as the same may vary in girth.
Figure 11:
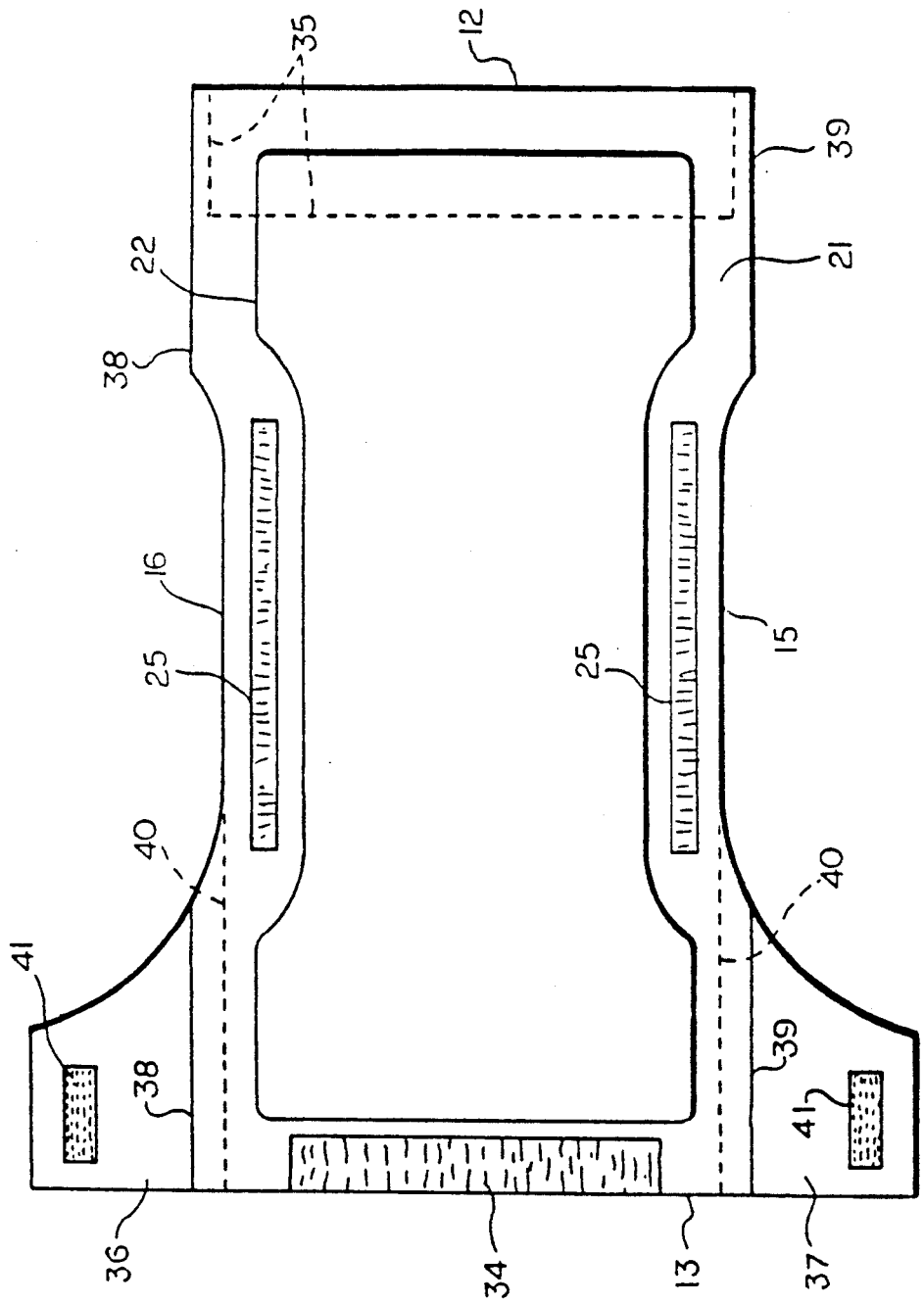
FIG. 11 is a plan view of the inner face of a disposable diaper which incorporates a second embodiment of the invention.

A second embodiment of the invention is shown on FIGS. 11 and 12. The same or similar parts are identified with the same reference numeral, as used earlier herein. FIG. 11 is a view of the baby diaper in which the backsheet 11 is lowermost and the topsheet 21 is uppermost; in other words, on this view the inside surface of the garment is shown. The contour of the diaper is formed from a liquid-impermeable backsheet 11, a liquid-permeable topsheet 21 in facing superposed relation with the inner surface of the backsheet, and an absorbent body 22 is located between the backsheet 11 and topsheet 21. A waist elastic 34 is attached to rear waistband portion 13 of the overlying sheets 21 and 11 and arranged to shirr the waistband portion. Leg elastic members 25 are attached to the respective side margins 15 and 16 of the garment and configured to gather and shirr the leg band portions of the garment to seal about the leg of the wearer.

In this embodiment of the invention, the diaper includes opposite side panels 36 and 37 alternatively may be composed of a liquid-permeable material, may be elastic, or may be composed of plastic film. Side panels 36 and 37 are attached along longitudinal sides 38 and 39, respectively, of the composite topsheet and backsheet to provide the ear portions of the rear waistband of the diaper. The side panels may be attached in suitable overlapping fashion, their innermost edges 40 lying inboard and along line of the side margins 15 and 16.

A tab 41 of hook material is attached directly onto each of the side panels 36 and 37, preferably placed such that the long dimension (length) of the tab extends longitudinally of the garment (direction L on FIG. 1) and the short dimension (width) of the tab extends laterally (direction T) of the garment. The hook tab 41 may be on the order of 1 inch long and ½ inch wide. The tab 41 is adhesively bonded to the inner surface of the side panel facing upwardly, as shown on FIG. 11. The hook tab 41 is constructed of the hook material described earlier herein. Tab 41 may be heat bonded or sonic welded directly to the side panel material, or fastened by hot melt pressure-sensitive adhesive in its longitudinally oriented position on the diaper.

Under the construction described, alternatively the positioning of the hook material and loop material may be reversed. Loop material may be secured to tab 41, and the hook material may be secured to the diaper outer cover in proper placement thereon.

As shown on FIG. 12, the waist girth variable is enhanced in this embodiment by the fact the ear portions 36 and 37 of the diaper along the rear waistband may be brought together in substantially an abutting relationship to provide the minimum size or girth (see dotted outline) as contrasted with the maximum girth whereat the hook tabs 41 are placed at the extreme lateral edge of the loop material on patch 35. Also, the dimension of the hook tab in the girth direction (lateral direction on the diaper) is the smaller width dimension. This allows approximately a one to one and one-half inch gain in girth variable, yet the same area of hook fastener is being utilized for holding the waistband closed. And, the stress forces in the waistband are distributed over a wider band, that is a band width that is the same as the length of the hook tabs.

Figure 13:
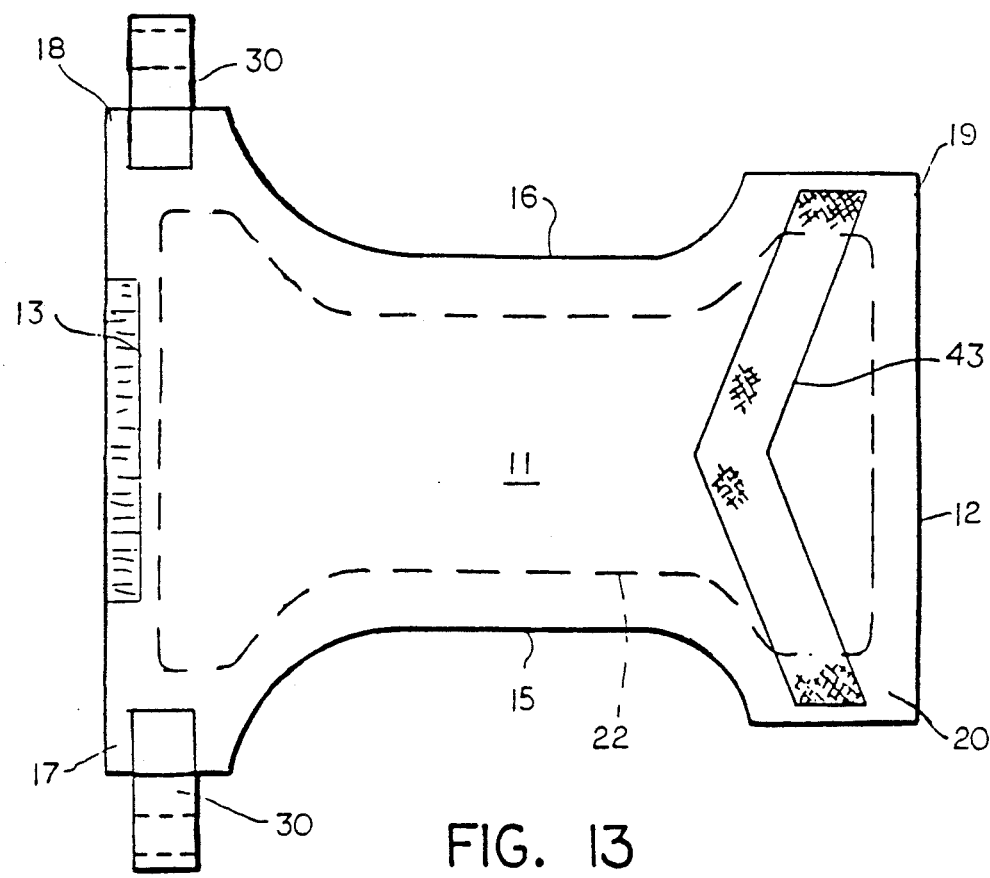
FIG. 13 is a plan view of the outer face of a disposable diaper which incorporates a third embodiment of the invention.

Referring to FIG. 13, the diaper incorporates the mechanical fastening system in which a chevron-shaped patch 43 of the loop material is adhesively bonded onto the outer surface of backsheet 11 by placement in the front waistband region 12 of the diaper. Chevron-shaped patch 43 provides an attachment zone for the hook tabs 30 at the rear waistband 13 which enhances the leg fit of the diaper on the wearer, yet minimizes the amount of the loop material used in the fabrication of the garment's attachment patch.

Figure 14:
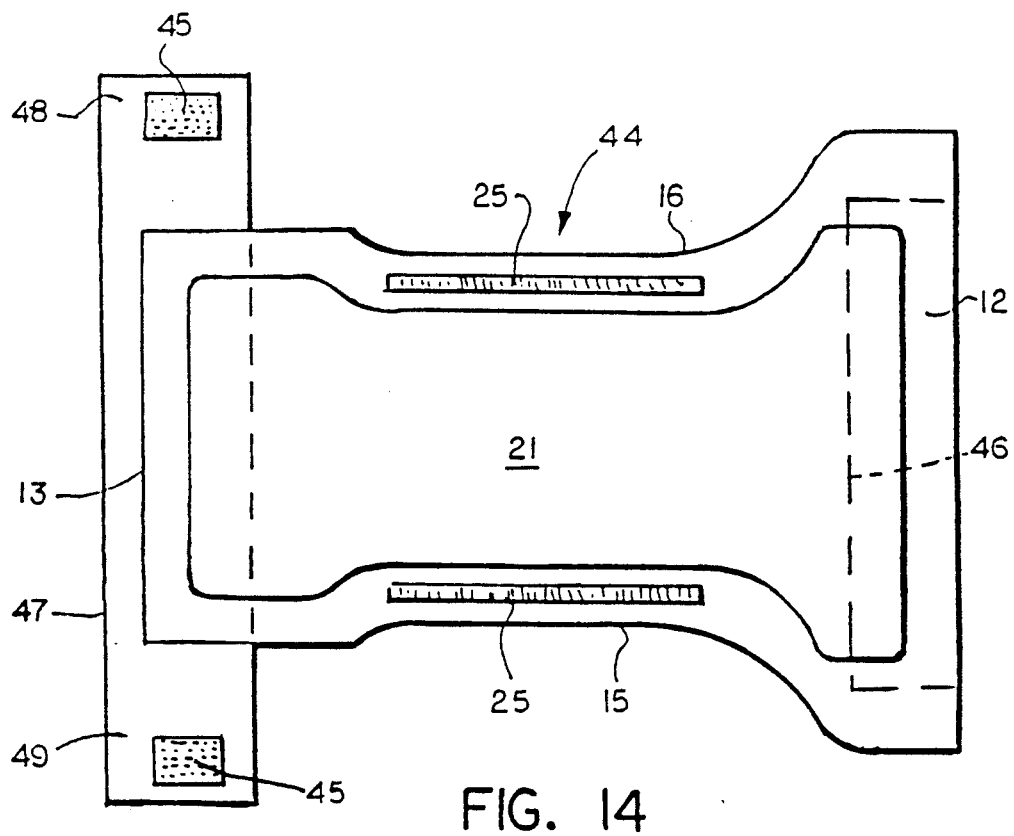
FIG. 14 is a plan view of the inner face of a disposable diaper that is placed next to the wearer's skin and which incorporates a fourth embodiment of the invention.
Figure 15:
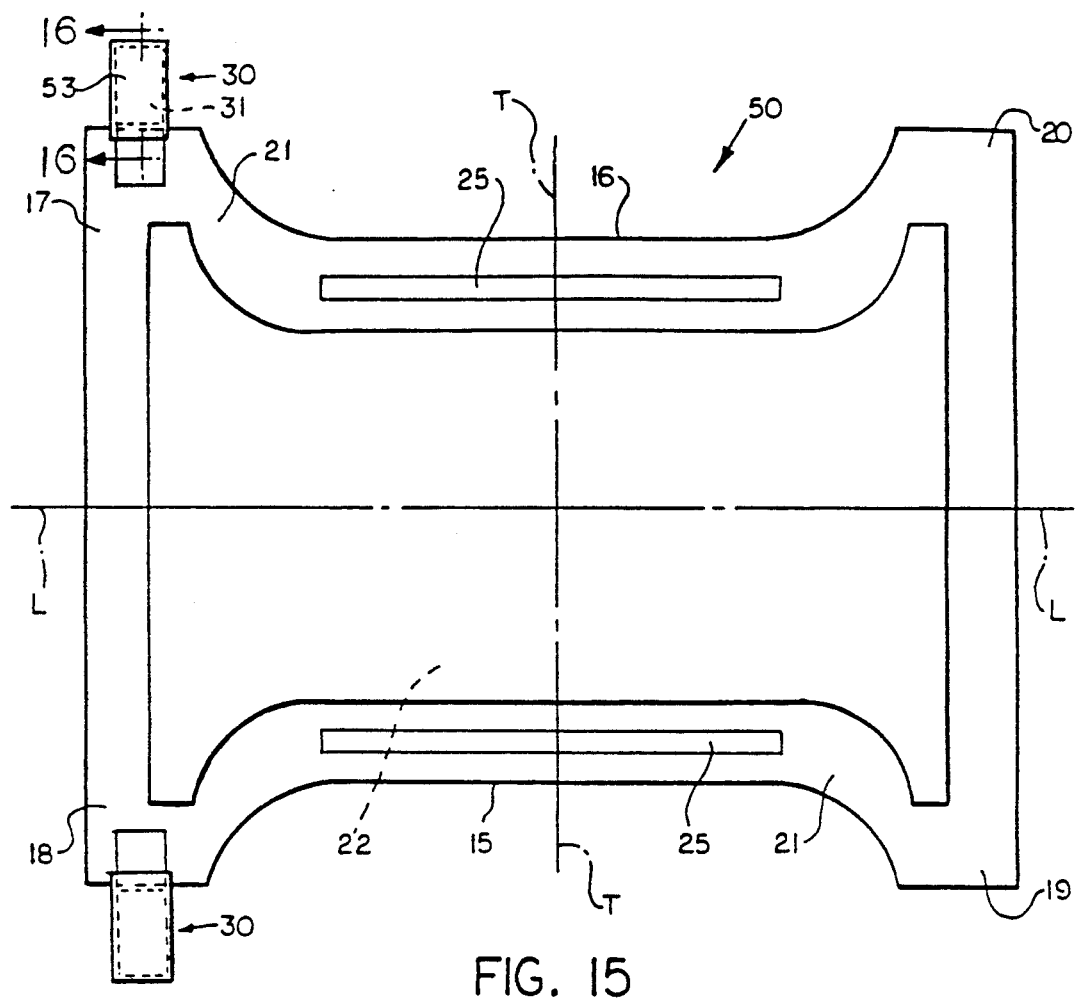
FIG. 15 is a plan view of the inner face of a disposable diaper which incorporates a fifth embodiment of the invention.
Figure 16:
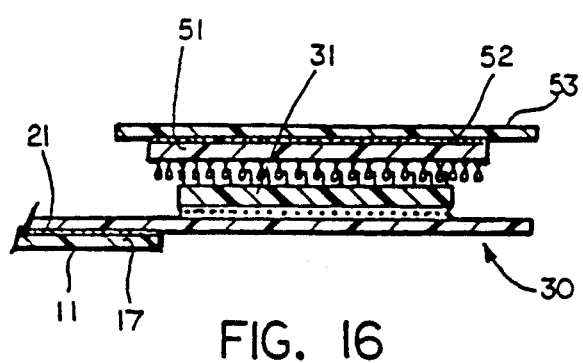
FIG. 16 is an enlarged sectional elevational view (partly schematic) taken along line 16–16 on FIG. 15.
Figure 17:
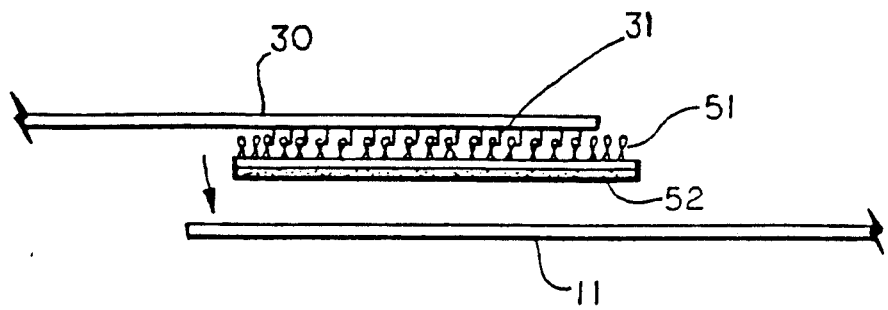
FIGS. 17–19 are sectional elevational views, partly schematic for ease of illustration, which show the diaper fastener system of FIGS. 15 and 16 in a succession being put into use on the first fastening (FIG. 17), in service with the waistband fastened (FIG. 18), and after the fastening system is released to open the waistband (FIG. 19).
Figure 18:
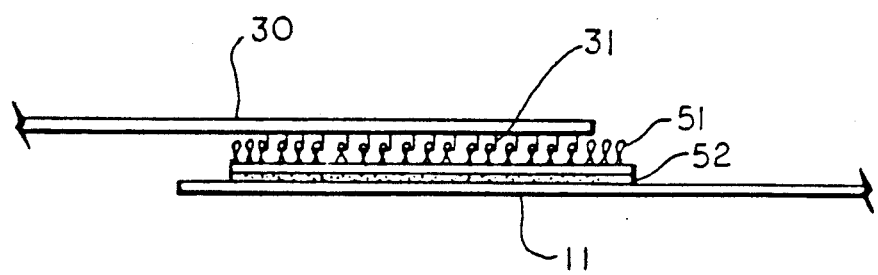
Figure 19:
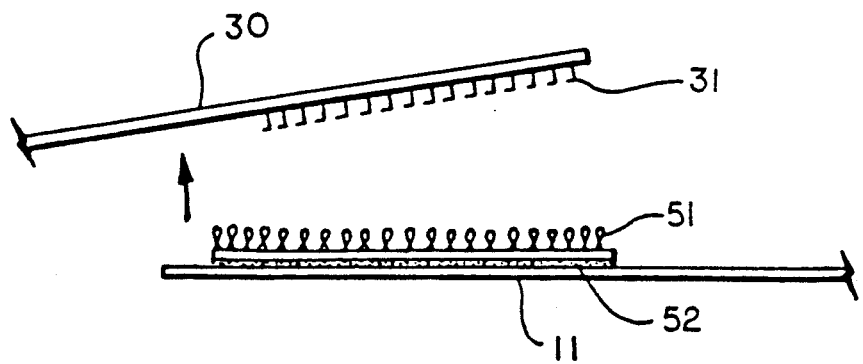

FIG. 14 illustrates a further embodiment of the invention. The absorbent article 44 includes a liquid-impermeable backsheet 11, a liquid-permeable topsheet 21 located in facing relationship with the inner surface of the backsheet and an absorbent body 22 is located between the topsheet and backsheet. A waist elastic member (not shown) may be arranged to shirr the front waistband 12. Leg elastic members 25 are attached at the side margins 15 and 16, respectively, configured to gather and shirr the leg margins of the garment to form seals or gaskets about the leg of the wearer. A rear waistband portion 47 is attached along the rear margin 13 such that the ends 48 and 49 of waistband portion 47 extend outwardly to form ears. The mechanical fastener components, earlier described, are attached to the diaper, such as, the hook tabs 45 are adhesively attached in each of the ears 48 and 49 of waistband 47. The hooks of the hook material extend in the direction of the body of the wearer to be attached on the patch 46 of loop material adhesively connected on the outside surface of backsheet 11 at the front waistband 12. As shown, the waistband 47 is adhesively attached to overlap the marginal edge at 13 of the article and extend longitudinally outwardly along the L axis of the diaper. The waistband 47 may be made of an elastomeric material to provide an elastic component of the waistband. The hook tabs 45 are attached onto the material of the ears 48 and 49 to face inwardly (as shown on FIG. 14) in the fashion described for FIG. 11. The long dimension of the hook tab is shown as parallel with the longitudinal axis L of the diaper, however, the tab 45 may be alternatively fastened thereon such that its long dimension extends transversely (direction T) of the diaper 44.

FIGS. 15-19 show a further embodiment of the invention wherein the hook and loop fastening system is employed having the loop material, as part of a target patch, which may be placed selectively on the outer cover by the user upon first use of the garment. The absorber article 50 is a disposable diaper shaped and constructed similarly to the diaper shown on FIGS. 1-4 described earlier herein. The hook tabs 30 are connected to the ear portions 17 and 18 at the rear waistband of the diaper in the manner described such that the hooks of the tabs face upwardly (inwardly of the diaper as viewed on FIG. 2). In the fabrication of the diaper 50, a target patch 51 of loop material is releasably attached to hook material 31 of the tab 30, as shown on FIG. 16. A pressure-sensitive adhesive layer 52 is constructed on the patch 51 at its surface opposite the loops. When stored on the diaper, adhesive layer 52 is positioned against a release layer, such as a piece of release paper 53, to prevent the adhesive from fastening itself in random, unwanted fashion. Optionally, the release layer may comprise an inboard portion of tab 30 treated with a release coating against which adhesive layer 52 rests when tab 30 is inwardly folded to its storage position.

During use, the release paper 53, if used, is manually removed and the composite assembly comprising tab 30,31 and target patch 51,52 is positioned in a desired fastening position against the outer surface of backsheet 11. Adhesive layer 52 then secures the target patch to the surface of outer cover 11 (See FIGS. 17-18). Adhesive layer 52 is sufficiently strong such that the target patch 51 remains adhered to the outer surface of the diaper when hook material 31 on the tab is pulled away from the loop material of patch 51 (See FIG. 19). Thereafter, the hook tab 30,31 can be refastened against the loop material of patch 51 now adhesively attached onto the backsheet 11 of the diaper in the initial placement position. Pressure-sensitive adhesive tape materials for constructing the loop material patch 51, as described, are available from 3M Company, St. Paul, Minnesota. The tape adhesive preferably has an average peel adhesion force of at least about 11.7N. Peel force values may be determined in accordance with procedures of ASTM-D1876-72, referenced above herein.

Having described various embodiments of the invention in detail, it will be readily apparent to those ordinarily skilled in the art that various changes and modifications may be made without departing from the scope of the invention as set forth in the appended claims.

It is claimed:

1. An absorbent article having superposed backsheet, absorbent body and topsheet elements fastened together as an elongated composite of select shape,
    opposite longitudinal end portions of said composite providing first and second waistband portions, respectively, adapted to overlap each other to encircle a user's body,
    a pair of ear portions disposed at the opposite ends of said first waistband portion,
    a means for fastening the first and second waistband portions to each other in said overlapping relationship, comprising:
    a hook and loop mechanical fastener of interlocking materials located on each ear portion, each mechanical fastener comprising a first component and a second component with each first component having a surface for releasably engaging a surface of said second component,
    said first component of a one of said mechanical fasteners being attached to each of said ear portions at a surface of said first component which is opposite the engaging surface thereof, with each first component having a target patch of said second component releasably engaged therewith,
    each target patch of said second component having a pressure-sensitive adhesive on its surface opposite said engaging surface thereof, said pressure-sensitive adhesive constructed for storage positioning against a release layer and adapted to separate from said release layer to selectively attach said second component to the composite on its second waistband portion and secure the first and second waistband portions about the body of the user,
    with said engaging surfaces of said first and second components thereby releasably attaching the first and second waistband portions about the body of the user.

2. The absorbent article of claim 1 in which there is included a layer of releasable material overlying the said adhesive on the surface of the other component adapted to be removed for thereafter adhesively attaching the other component onto said composite thereby closing the first and second waistband portions.

3. The absorbent article of claim 1 wherein said first component comprises a hook material and said second component comprises a loop material, said hook material being adhesively attached to said ear portions at a surface of the first component which is opposite the hooks thereof,
    said loop material having said pressure-sensitive adhesive layer on its surface opposite the loops thereof for attaching the loop material to the front waistband upon initial closing of the waistband portions.

4. An article as recited in claim 1, wherein said hook material comprises a polymeric base material of about 0.008-0.01 inch thickness having a flexural modulus of about 70,000 to 120,000 psi, a Shore hardness of about D-40-D-80, and the hook configurations thereof being tapered base to tip, and having a caliper in the range of about 0.035 to 0.050 inch.

5. The article of claim 4, wherein the hook design is tapered base to tip with the tips of the hooks rounded with a radius, and wherein the hook material has a total caliper in the range of about 0.04 to 0.05 inches, a hook density within the range of about 440 to 1040 hooks per square inch, a row density within the range of about 20-60 rows per inch, and a base film with a thickness within the range of about 0.008-0.010 inch.

6. An article as recited in claim 1, wherein said loop material comprises a knit fabric composed of fabric yarns, about 15%-35% of the fabric yarns having 1-15 filaments per yarn and a yarn denier within the range of about 15-30d, and about 65%-85% of the fabric yarns having about 10-30 filaments per yarn and a yarn denier within the range of about 30-50d.

7. The article of claim 6, wherein said fabric is a two-bar warp knit fabric in which the courses of the warp knit are about 21-41 per inch and the wales of said warp knit are about 26-46 per inch.

8. The article of claim 7 in which the caliper of said fabric is in the range of about 0.01 to 0.04 inches.

9. The article of claim 8 in which the basis weight of said fabric is in the range of about 1 to 3 ounces per square yard.

10. The article of claim 9 in which said fabric is a polyethylene-terephthalate tricot fabric of raised loop construction and comprises approximately 26% of yarn of denier within the range of about 15-30d and approximately 74% of yarn of denier of about 30-50d; the courses of the fabric are about 31 per inch and the wales are about 36 per inch; and the basis weight of the fabric is approximately 1.6 ounces per square yard.

11. An absorbent article having superposed backsheet, absorbent body and topsheet elements fastened together in a selected shape,
a pair of separate ear portions,
means for attaching said ear portions at laterally opposed sides of said shape and adjacent one longitudinal end thereof to form a composite,
the opposite longitudinal ends of said composite providing front and rear waistband portions, respectively, adapted to overlap each other near their lateral ends upon encircling the abdomen of the user,
a means for fastening the front and rear waistband portions to each other in said overlapping relationship, comprising:
a hook and loop fastener comprising two interlocking materials, one being a hook material and the other being a loop material,
said hook material being attached to each of said ear portions, and the loop material being attached at the opposite longitudinal end of the composite,
said hook material comprising a polymeric base material of about 0.008-0.01 inch thickness having a flexural modulus of about 70,000 to 120,000 psi, a Shore hardness of about D-40-D-80, and the hook configurations thereof being tapered base to tip, and having a caliper in the range of about 0.035 to 0.050 inch,
said hook and loop materials being engageable to releasably attach the front and rear waistband portions to each other to encircle the abdomen of the user.

12. The article of claim 11, wherein the hook design is tapered base to tip with the tips of the hooks rounded with a radius, and wherein the hook material has a total caliper in the range of about 0.04 to 0.05 inches, a hook density within the range of about 440 to 1040 hooks per square inch, a row density within the range of about 20-60 rows per inch, and a base film with a thickness within the range of about 0.008-0.010 inch.

13. The article of claim 11 in which the loop material is located in the proximity of the outer lateral edge of the composite and in the other waistband portion.

14. The absorbent article of claim 11 in which said loop material is a patch of selected geometric configuration that is fastened to the outer cover in the proximity of the other said waistband portion.

15. The absorbent article of claim 14 wherein said patch is rectangular in shape.

16. The absorbent article of claim 14 wherein said patch is a chevron-shape.

17. The absorbent article of claim 16 wherein said chevron patch has its apex disposed toward the longitudinal center of said outer cover.

18. The article of claim 11, wherein said separate ear portions are elastomeric.

19. An absorbent article having superposed backsheet, absorbent body and topsheet elements fastened together in a selected shape,
a pair of separate ear portions,
means for attaching said ear portions at laterally opposed sides of said shape and adjacent one longitudinal end thereof to form a composite,
the opposite longitudinal ends of said composite providing front and rear waistband portions, respectively, adapted to overlap each other near their lateral ends upon encircling the abdomen of the user,
a means for fastening the front and rear waistband portions to each other in said overlapping relationship, comprising:
a hook and loop fastener comprising two interlocking materials, one being a hook material and the other being a loop material,
said hook material being attached to each of said ear portions, and the loop material being attached at the opposite longitudinal end of the composite,
said loop material comprising a knit fabric composed of fabric yarns, about 15%-35% of the fabric yarns having 1-15 filaments per yarn and a yarn denier within the range of about 15-30d, and about 65%-85% of the fabric yarns having about 10-30 filaments per yarn and a yarn denier within the range of about 30-50d,
said hook and loop material being engageable to releasably attach the front and rear waistband portions to each other to encircle the abdomen of the user.

20. The article of claim 19, wherein said fabric is a two-bar warp knit fabric in which the courses of the warp knit are about 21-41 per inch and the wales of said warp knit are about 26-46 per inch.

21. The article of claim 20 in which the caliper of said fabric is in the range of about 0.01 to 0.04 inches.

22. The article of claim 21 in which the basis weight of said fabric is in the range of about 1 to 3 ounces per square yard.

23. The article of claim 22 in which said fabric is a polyethylene-terephthalate tricot fabric of raised loop construction and comprises approximately 26% of yarn of denier within the range of about 15-30d and approximately 74% of yarn of denier of about 30-50d; the courses of the fabric are about 31 per inch and the wales are about 36 per inch; and the basis weight of the fabric is approximately 1.6 ounces per square yard.

* * * * *